United States Patent [19]
Cussell

[11] 3,993,081
[45] Nov. 23, 1976

[54] ENDOTRACHEAL TUBE HOLDER

[75] Inventor: George A. Cussell, Columbus, Ga.

[73] Assignee: Swesco Inc., Tucker, Ga.

[22] Filed: Jan. 23, 1975

[21] Appl. No.: 543,472

[52] U.S. Cl. .......................... 128/351; 128/DIG. 26
[51] Int. Cl.² ................. A61M 16/00; A61M 25/02
[58] Field of Search ............. 128/346, 351, DIG. 26

[56] References Cited
UNITED STATES PATENTS

| | | | |
|---|---|---|---|
| 2,468,823 | 5/1949 | Housepian | 128/346 |
| 2,727,512 | 12/1955 | Muller | 128/DIG. 26 |
| 2,820,457 | 1/1958 | Phillips | 128/351 |
| 2,898,917 | 8/1959 | Wallace | 128/DIG. 26 |
| 3,176,690 | 4/1965 | H'Doubler | 128/DIG. 26 |
| 3,247,852 | 4/1966 | Schneider | 128/346 |
| 3,585,997 | 6/1971 | Ancerewicz | 128/351 X |
| 3,682,166 | 8/1972 | Jacobs | 128/145.8 |
| 3,730,187 | 5/1973 | Reynolds | 128/DIG. 26 |
| 3,794,026 | 2/1974 | Jacobs | 128/145.8 |

*Primary Examiner*—Channing L. Pace
*Attorney, Agent, or Firm*—Newton, Hopkins & Ormsby

[57] ABSTRACT

An endotracheal tube holder is disclosed comprising a clamp having a primary passageway through which an endotracheal tube may be passed in frictional engagement, and a plurality of secondary passageways. A strip of adhesive tape is provided adapted to be secured to human skin and having a plurality of holes. The holder further includes elongated flexible tying means sized for passage through the clamp secondary passageways and through the tape holes for securing the clamp to the tape.

5 Claims, 5 Drawing Figures

ENDOTRACHEAL TUBE HOLDER

BACKGROUND OF THE INVENTION

Heretofore, endotracheal tube holders have been held in position on patients by varying means. For example, they have been directly secured to oral cavities themselves by the use of holding means inserted partially into the oral cavity itself about either side of the cavity orifice as disclosed in U.S. Pat. No. 3,139,088. Other endotracheal tube holders have employed a clamp for holding the tube to which is attached a band adapted to be secured about the head or the neck of the patient to maintain the clamp and thus the tube in place. U.S. Pat. Nos. 3,602,227 and 3,760,811 exemplify these types of holders. Yet other tube holding means have employed ear encircling looped bands coupled with the tube in holding it in place.

While the just mentioned types of endotracheal tube holders have proven effective for adult patient use, they often have failed to hold endotracheal tubes securely in place on infants. The twisting and turning of infant patients often causes head, neck or ear encircling straps to become dislodged thereby enabling the tube itself to become mislocated or even ejected completely from the patient. Other holders have not been readily adjusted or reused. The structural complexity and attendant manufacturing cost of still others has been excessive.

Accordingly, it is a general object of the present invention to provide an improved endotracheal tube holder.

More specifically, it is an object of the present invention to provide an endotracheal tube holder which may be effectively used upon infant patients.

Another object of the invention is to provide an endotracheal tube holder having improved means for securing the tube holder itself to the patient.

Another object of the invention is to provide an endotracheal tube holder through which a tube may be easily secured and readily adjusted.

Yet another object of the invention is to provide an endotracheal tube holder which is easily secured to a patient without the necessity for head, neck or ear encircling bands for securing the holder itself to the patient.

Still another object of the invention is to provide an endotracheal tube holder of the type described which is relatively inexpensive to construct and assemble and which may be composed of readily available and relatively simple structural components.

SUMMARY OF THE INVENTION

In one form of the invention, an endotracheal tube holder is provided comprising a clamp defining a primary passageway through which an endotracheal tube may be placed in snug, frictional engagement and a plurality of secondary passageways. A strip of adhesive tape adapted to be secured to human skin is provided having a plurality of holes. Elongated flexible tying means is also provided sized for passage through the clamp secondary passageways and through the tape holes in securing the clamp to the tape and thus in turn to the patient.

In another form of the invention, an endotracheal tube holder is provided comprising a clamp having a pair of elongated jaws hinged together at one end and releasably latched together at the other end. The clamp defines at least one passageway through which an endotracheal tube may be placed in snug, frictional engagement with the clamp other end latched together. The holder also includes a resilient pad having at least one passageway through which the tracheal tube may be passed from the clamp passageway into the patient.

DETAILED DESCRIPTION OF THE DRAWING

Figure 1:
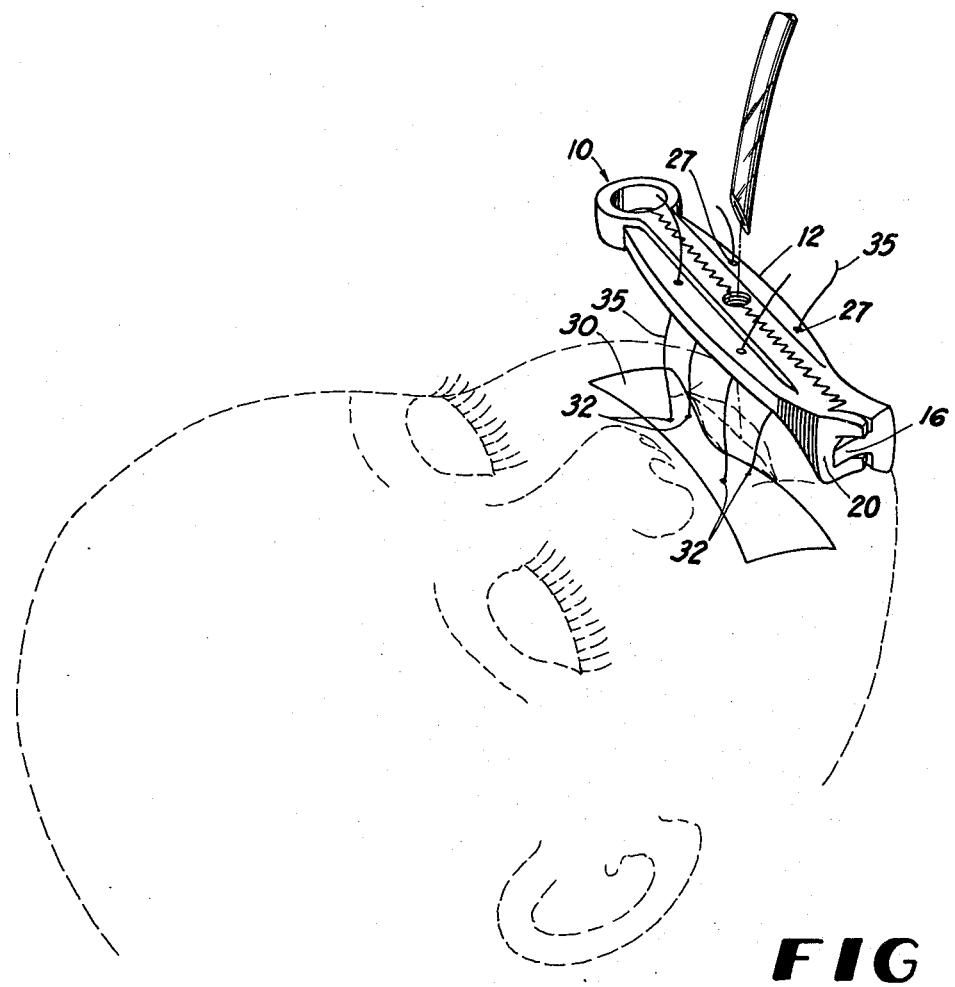
FIG. 1 is an exploded view, in perspective, of an endotracheal tube holder embodying principles of the invention in one preferred form shown positioned for attachment to an infant patient whose head is shown in outline form.
Figure 2:
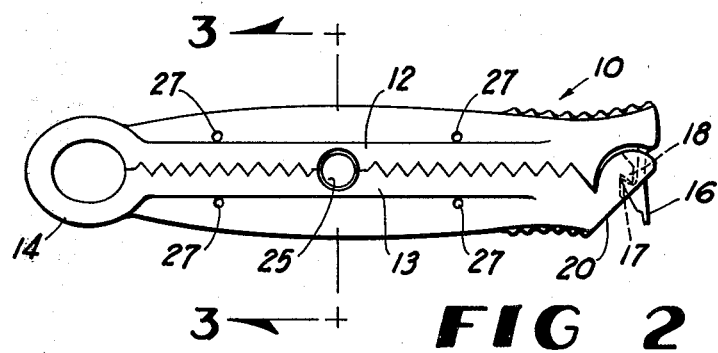
FIG. 2 is a front view, in elevation, of a clamp component of the endotracheal tube holder illustrated in FIG. 1.
Figure 3:
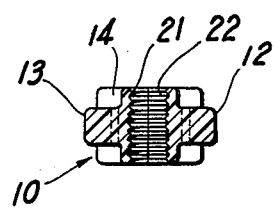
FIG. 3 is a cross-sectional view of the endotracheal tube holder clamp shown in FIG. 1 taken along plane 3—3.

Referring now in more detail to the drawing, there is shown in FIGS. 1–3 an endotracheal tube holder comprising a modified Hollister plastic umbilical clamp 10 having a pair of elongated jaw members 12 and 13. Each jaw member has a set of sawtooth teeth disposed relative to each other for intermeshing mutual engagement. The two jaw members are unitarily joined together by a flexible annular hinge member 14 on one end while the other end is provided with latching means which include a flexible pendant 16 having a pointed projection 17 depending from one jaw member and adopted to be seated within a mating, V-shaped recess formed in an end of the other jaw member adjacent a protrusion 18.

So far described the holder clamp component is a standard Hollister type umbilical clamp. The clamp here, however, is seen further to have several modifications including a bevelled end 20 on jaw member 13 adjacent the latch. This is provided to facilitate unlatching of the latch by providing thumb accomodating space between end 20 and pendant 16 whereby the clamp may be used a number of times. The clamp is further seen to be provided with a generally cylindrical, central or primary passageway 25 the walls of which are formed of a succession of annular ridges 21 and annular troughs 22 as seen most clearly be reference to FIGS. 1 and 3. It will be further seen that half of this passageway is provided by a wall of one jaw member while the other half of the passageway is provided by a wall formed in the other jaw member. The clamp is further seen to include four secondary passageways 27 of relatively small size in comparison to the primary passageway which secondary passageways are disposed about and parallel with the primary passageway.

With continued reference to FIG. 1, the tube holder is also seen to include a strip of adhesive tape 30 having a peripheral edge shaped to be secured to the moustache area of a patient between the patient's upper lip and nose. The tape is provided with four holes 32 positioned for registry with secondary holes 27 in the clamp. The holder is seen further to include a pair of silk suture filaments 35 which are looped through adjacent tape holes 32 and through the two pairs of clamp secondary passageways respectively.

In using the just described endotracheal tube holder the patient's moustache area is preferably painted with a tincture of benzoin and then covered with the adhesive tape. The two suture filaments are then looped through adjacent holes 32 in the tape and the tape secured to the painted moustache skin area. With the jaws of the clamp opened an endotracheal tube is seated in the semi-cylindrical passageway of one jaw and the other jaw then snapped closed and latched by disposing flexible pendant 16 in the recess of the other jaw member thereby frictionally seating and gripping that portion of the tube which passes through the primary passageway 25. The tube is then inserted into the patient's oral cavity and the sutures protruding from the tape passed through secondary passageways 27 of the clamp. With the clamp now positioned flush with the tape the exposed ends of the sutures are tied together. If desired, a wax pencil mark may be used to mark the tube adjacent the surface of the clamp distal the patient in order that attendants or nurses may easily check to insure that the tube is remaining in proper position. Such a mark may also serve as a guide if repositioning of the tube is subsequently found to be desired.

Figure 4:
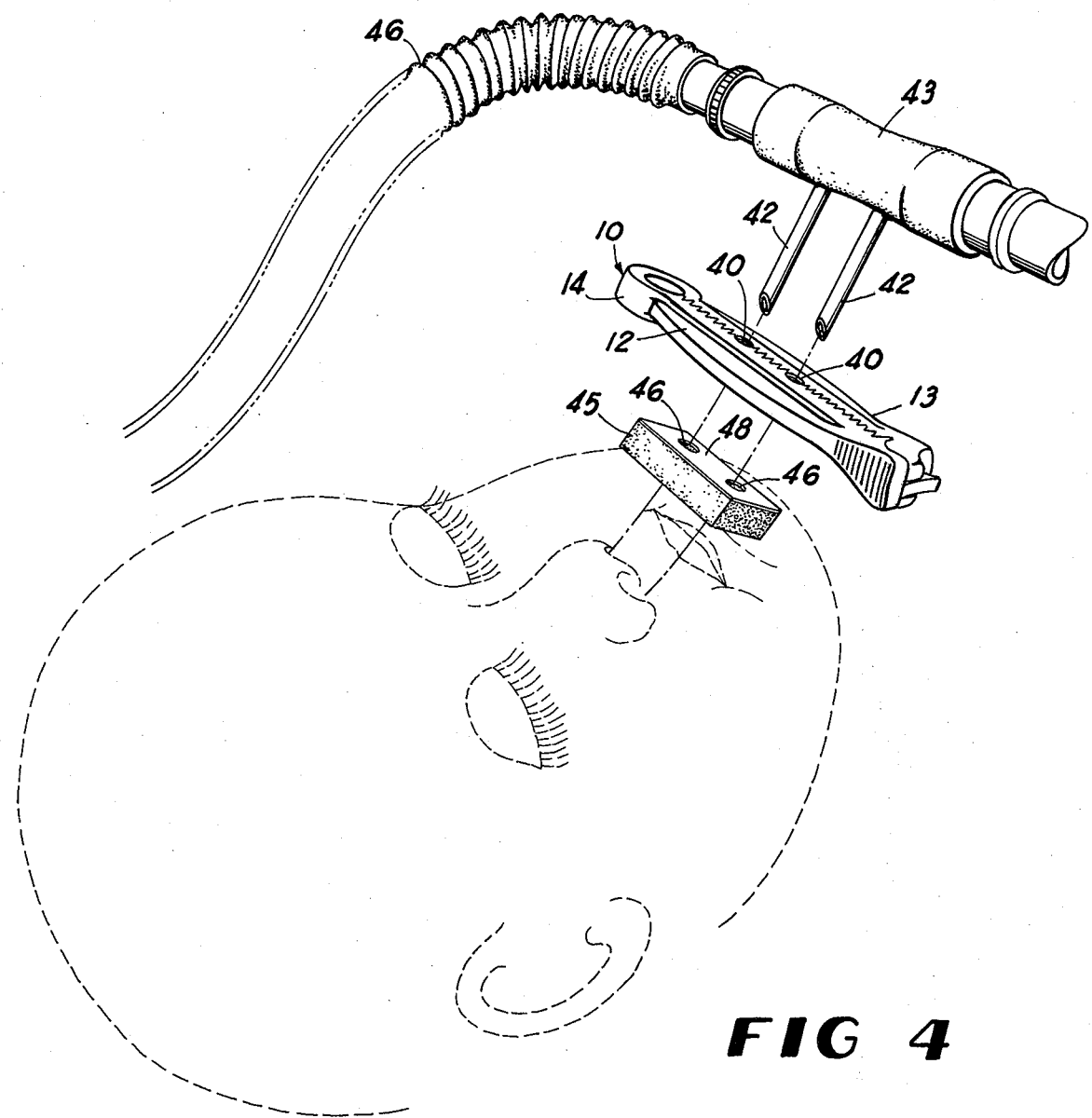
FIG. 4 is an exploded view, in perspective, of an endotracheal tube holder embodying principles of the invention in another preferred form shown positioned for attachment to a patient whose head is shown in outline form.
Figure 5:
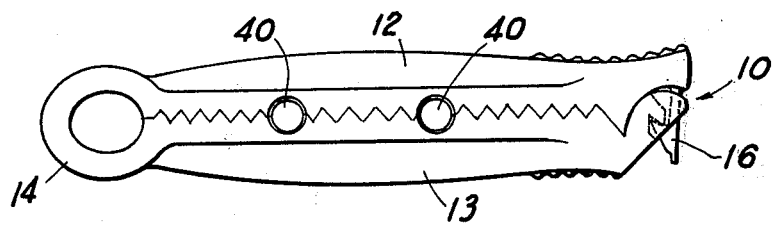
FIG. 5 is a front view, in elevation, of a clamp component of the endotracheal tube holder illustrated in FIG. 4.

In FIGS. 4 and 5 an alternative embodiment is shown in which a Hollister type plastic umbilical clamp is again used in modified form as a component of an endotracheal tube holder. In this embodiment the clamp is provided with two ridged passageways 40 sized to frictionally receive and engage two parallel endotracheal tubes 42 coupled together by a fitting 43. A resilient pad 45 is also provided having a pair of passageways 46 formed therethrough and spaced apart a distance to be in register with the pair of passageways 40 of the clamp when the clamp is pressed to a surface 48 of the resilient pad distal the patient. In this case the holder is secured to the patient by exteriorly gripping a pair of flexible hoses 46 which extend from influid communication with coupling 43. This may be done by passing the two flexible hoses through holes or clamps held to opposite sides of the patient's bed in conventional fashion.

It thus is seen that an endotracheal tube holder is provided that is partially made of readily available medical components such as a modified Hollister umbilical clamp, adhesive tape, and sutures. The holder is capable of securing both the endotracheal tube to the holder as well as the holder itself to the patient. With this capability the tube does not readily become dislodged from its proper position within the oral cavity of the patient. The holder is easy to install, adjusts to be reused. It does not necessarily require the inclusion of patient head, neck or ear wrap around bands or attachment means. The holder is also relatively inexpensive to manufacture and may be used with a minimum of training.

While only two embodiments have been illustrated in the drawing, it should be clearly understood that they merely serve to illustrate two preferred forms of the invention. Many modifications, additions or deletions may, of course, be made thereto without departure from the spirit and scope of the invention as set forth in the following claims.

I claim:

1. An endotracheal tube holder comprising, in combination, a clamp defining a primary passageway through which an endotracheal tube may be placed in snug frictional engagement and a plurality of secondary passageways through which tying means may be passed; a strip of adhesive tape adapted to be secured to human skin and having a plurality of holes through which the tying means may also be passed; and elongated flexible tying means passing through said clamp secondary passageways and through said tape holes and securing said clamp to said tape, said tape being the sole means adapted to be secured to human skin.

2. An endotracheal tube holder in accordance with claim 1 wherein said clamp secondary passageways are located in a first pattern about said primary passageway, wherein said adhesive tape holes are located in a second pattern, and wherein said first and second patterns are substantially the same whereby the clamp is secured to the adhesive tape with the clamp secondary passageways substantially aligned with the tape holes.

3. An endotracheal tube holder in accordance with claim 1 wherein said clamp primary passageway is at least partially defined by a succession of annular ridges and annular troughs.

4. An endotracheal tube holder in accordance with claim 1 wherein said clamp comprises a pair of elongated jaws hinged together at one end and including means for latching the jaws together at this other end.

5. An endotracheal tube in accordance with claim 4 wherein each of said jaws is elongated in a direction substantially normal said clamp primary and secondary passageways.

* * * * *